(12) United States Patent
Tessien

(10) Patent No.: US 7,500,777 B2
(45) Date of Patent: Mar. 10, 2009

(54) METHOD AND APPARATUS FOR MONITORING TEMPERATURE DIFFERENCES WITHIN A CAVITATION CHAMBER

(75) Inventor: Ross Alan Tessien, Nevada City, CA (US)

(73) Assignee: Impulse Devices, Inc., Grass Valley, CA (US)

( * ) Notice: Subject to any disclaimer, the term of this patent is extended or adjusted under 35 U.S.C. 154(b) by 204 days.

(21) Appl. No.: 11/235,879

(22) Filed: Sep. 26, 2005

(65) Prior Publication Data

US 2007/0234808 A1 Oct. 11, 2007

Related U.S. Application Data

(63) Continuation of application No. 11/226,641, filed on Sep. 14, 2005.

(51) Int. Cl.
*B01F 11/00* (2006.01)
*B01F 15/06* (2006.01)

(52) U.S. Cl. .................. 366/108; 366/115; 366/145

(58) Field of Classification Search .............. 366/144, 366/108, 114, 115, 145, 146; 203/2
See application file for complete search history.

(56) References Cited

U.S. PATENT DOCUMENTS

| | | | | |
|---|---|---|---|---|
| 2,022,809 A | * | 12/1935 | Kramer | .................. 203/2 |
| 2,176,500 A | * | 10/1939 | Hyatt | .................. 203/15 |
| 2,299,899 A | * | 10/1942 | Houghland | .................. 203/2 |
| 4,333,796 A | | 6/1982 | Flynn | |
| 4,563,341 A | | 1/1986 | Flynn | |
| 5,659,173 A | | 8/1997 | Putterman et al. | |
| 5,858,104 A | | 1/1999 | Clark | |
| 5,968,323 A | | 10/1999 | Pless | |

(Continued)

FOREIGN PATENT DOCUMENTS

WO PCT/US95/15972 7/1996

(Continued)

OTHER PUBLICATIONS

Blake et al, Acoustic Cavitation:The Fluid Dynamics of Non-Spherical Bubbles, Phil. Trans. R. Soc. Lond. A, 1999, pp. 251-267, vol. 357, Publisher: The Royal Society, Published in: Great Britain.

(Continued)

*Primary Examiner*—David L Sorkin
(74) *Attorney, Agent, or Firm*—C. Brandon Browning; Maynard Cooper & Gale, PC

(57) ABSTRACT

A method and apparatus for monitoring a temperature difference between two regions within a cavitation system is provided. The system's cavitation chamber is partially or completely filled with cavitation fluid, the amount that the system is filled controlling whether a cavitation fluid free surface is formed within the cavitation chamber or a conduit coupled to the chamber. Regardless of whether the region of the system above the cavitation fluid free surface is within the chamber or within the conduit, a temperature difference is created between this region and the cavitation fluid within the cavitation chamber. The temperature difference between these two regions is monitored by monitoring the temperature of each region. The temperature difference can be created by either heating the region above the cavitation fluid free surface, cooling the cavitation fluid, or both.

20 Claims, 3 Drawing Sheets

U.S. PATENT DOCUMENTS

| | | | |
|---|---|---|---|
| 6,193,849 B1 * | 2/2001 | Lockett, Jr. | 203/2 |
| 6,361,747 B1 | 3/2002 | Dion et al. | |
| 2002/0090047 A1 | 7/2002 | Stringham | |

FOREIGN PATENT DOCUMENTS

| | | |
|---|---|---|
| WO | PCT/US02/16761 | 12/2002 |
| WO | PCT/CA03/00342 | 9/2003 |

OTHER PUBLICATIONS

M. Dan et al., Ambient Pressure Effect on Single-Bubble Sonoluminescence, Physical Review Letters, Aug. 30, 1999, pp. 1870-1873, vol. 83, No. 9, Publisher: The American Physical Society, Published in: US.

Moss et al., Computed Optical Emissions from a Sonoluminescing Bubble, Physical Review E, Mar. 1999, pp. 2986-2992, vol. 59, No. 3, Published in: US.

Y.T. Didenko et al., Effect of Noble Gases on Sonoluminescence Temperatures during Multibubble Cavitation, Physical Review Letters, Jan. 24, 2000, pp. 777-780, vol. 84, No. 4, Publisher: The American Physical Society, Published in: US.

Gaitan et al, Experimental Observations of Bubble Response and Light Intensity Near the Threshold for Single Bubble Sonoluminescence, Physical Review E, May 1999, pp. 5495-5502, vol. 59, No. 5, Published in: US.

Barber et al, Sensitivity of Sonoluminescence to Experimental Parameters, Physical Review Letters, Feb. 28, 1994, pp. 1380-1382, vol. 72, No. 9.

F.R. Young, Sonoluminescence from Water Containing Dissolved Gases, J. Acoust. Soc. Am., Jul. 1996, pp. 100-104, vol. 60, No. 1, Publisher: Acoustical Society of America, Published in: US.

Putterman, Sonoluminescence:Sound Into Light, Scientific American, Feb. 1995, pp. 46-51.

Gaitan et al, Sonoluminescence and Bubble Dynamics for a Single, Stable, Cavitation Bubble, J. Acoust. Soc. Am., Jun. 1992, pp. 3166-3183, vol. 91, No. 6, Publisher: Acoustical Society of America.

Crum, Sonoluminescence, Physics Today, Sep. 1994, pp. 22-29, Publisher: American Institute of Physics, Published in: US.

Bollinger, Ultra Cavitation, http://wiretap.area.com/Gopher/Library/Article/Sci/cavitate.ult, Sep. 17, 2001, pp. 1-26.

* cited by examiner

METHOD AND APPARATUS FOR MONITORING TEMPERATURE DIFFERENCES WITHIN A CAVITATION CHAMBER

CROSS-REFERENCES TO RELATED APPLICATIONS

This application is a continuation of U.S. patent application Ser. No. 11/226,641 filed Sep. 14, 2005, the disclosure of which is incorporated herein by reference for any and all purposes.

FIELD OF THE INVENTION

The present invention relates generally to cavitation systems and, more particularly, to a cavitation system which includes a free cavitation fluid surface.

BACKGROUND OF THE INVENTION

Sonoluminescence is a well-known phenomena discovered in the 1930's in which light is generated when a liquid is cavitated. Although a variety of techniques for cavitating the liquid are known (e.g., spark discharge, laser pulse, flowing the liquid through a Venturi tube), one of the most common techniques is through the application of high intensity sound waves.

In essence, the cavitation process consists of three stages; bubble formation, growth and subsequent collapse. The bubble or bubbles cavitated during this process absorb the applied energy, for example sound energy, and then release the energy in the form of light emission during an extremely brief period of time. The intensity of the generated light depends on a variety of factors including the physical properties of the liquid (e.g., density, surface tension, vapor pressure, chemical structure, temperature, hydrostatic pressure, etc.) and the applied energy (e.g., sound wave amplitude, sound wave frequency, etc.).

Although it is generally recognized that during the collapse of a cavitating bubble extremely high temperature plasmas are developed, leading to the observed sonoluminescence effect, many aspects of the phenomena have not yet been characterized. As such, the phenomena is at the heart of a considerable amount of research as scientists attempt to further characterize the phenomena (e.g., effects of pressure on the cavitating medium) as well as its many applications (e.g., sonochemistry, chemical detoxification, ultrasonic cleaning, etc.).

U.S. Pat. No. 4,333,796 discloses a cavitation chamber that is generally cylindrical although the inventors note that other shapes, such as spherical, can also be used. It is further disclosed that the chamber is comprised of a refractory metal such as tungsten, titanium, molybdenum, rhenium or some alloy thereof and the cavitation medium is a liquid metal such as lithium or an alloy thereof. The chamber is heated to a temperature greater than the melting temperature of the selected cavitation medium. The cavitation medium within the chamber does not completely fill the chamber, thus leaving a vapor-liquid interface within the chamber. The ambient pressure within the chamber is the hydrostatic pressure plus the gas pressure maintained above the vapor-liquid interface and the vapor pressure of the medium itself. In at least one disclosed embodiment, the desired gas pressure is obtained by coupling the chamber to an external source of deuterium. Projecting through both the outer housing and the cavitation chamber walls are a number of acoustic horns, each of the acoustic horns being coupled to a transducer which supplies the mechanical energy to the associated horn.

U.S. Pat. No. 4,563,341, a continuation-in-part of U.S. Pat. No. 4,333,796, discloses a slightly modified, cylindrical cavitation chamber. The chamber is surrounded by an external heating coil which allows the cavitation liquid, e.g., aluminum, within the chamber to be maintained at the desired operating temperature. The system is degassed prior to operation by applying a vacuum through a duct running through the cover of the chamber. During operation, a vapor-liquid interface is maintained within the chamber. Argon gas is admitted to the chamber through the duct in the cover of the chamber, thus allowing the operating pressure to be controlled.

U.S. Pat. No. 5,659,173 discloses a sonoluminescence system that uses a transparent spherical flask fabricated from Pyrex®, Kontes®, quartz or other suitable glass and ranging in size from 10 milliliters to 5 liters. The inventors disclose that preferably the liquid within the flask is degassed and the flask is sealed prior to operation. In one disclosed embodiment, the cavitation chamber is surrounded by a temperature control system, thus allowing the liquid within the chamber to be cooled to a temperature of 1° C. Techniques are disclosed to control the static pressure in the liquid, for example coupling the chamber to a piston or latex balloon. Bubbles are introduced into the cavitation fluid using a variety of techniques including dragging bubbles into the fluid, for example with a probe, and localized boiling.

U.S. Pat. No. 5,858,104 discloses a shock wave chamber partially filled with a liquid. The remaining portion of the chamber is filled with gas which can be pressurized by a connected pressure source. Acoustic transducers mounted in the sidewalls of the chamber are used to position an object within the chamber while another transducer delivers a compressional acoustic shock wave into the liquid. A flexible membrane separating the liquid from the gas reflects the compressional shock wave as a dilatation wave focused on the location of the object about which a bubble is formed.

U.S. Pat. No. 5,968,323 discloses a cavitation chamber filled with a low compressibility liquid such as a liquid metal. A sealed fluid reservoir is connected to the bottom of the cavitation chamber by a pipe. Both the chamber and the reservoir are contained within a temperature controlled container. By pressurizing or evacuating the reservoir, fluid can be forced into or withdrawn from the cavitation chamber. Fluid flow into or out of the chamber is aided by a vacuum pump and a pressurized gas source coupled to the top of the cavitation chamber. The system includes two material delivery systems for introducing materials or mixtures of materials into the chamber. One of the delivery systems is coupled to the bottom of the chamber and is intended for use with materials of a lower density than that of the cavitation liquid, thus causing the material to float upwards. The second delivery system is coupled to the top of the chamber and is intended for use with materials of a higher density than that of the cavitation liquid, thus causing the material to sink once introduced into the chamber.

PCT Application No. US02/16761 discloses a nuclear fusion reaction chamber which is partially filled with the desired cavitation fluid, such as deuterated acetone. Within the chamber are upper and lower members, preferably anchored to the chamber, that define a resonant cavity. In at least one disclosed embodiment, the chamber and upper/lower members are all fabricated from glass. The chamber volume above the cavitation fluid is evacuated to approximately the vapor pressure of the cavitation fluid. In a preferred embodiment, a refrigeration device maintains the reaction chamber at a sub-ambient temperature. In at least one disclosed embodiment, acoustic waves are used to pretension the liquid. After the desired state of tension is obtained, a cavitation initiation source, such as a neutron source, nucleates at least one bubble within the liquid, the bubble having a radius greater than the critical bubble radius. The nucleated bubbles are then imploded, the temperature generated by the implosion being sufficient to induce a nuclear fusion reaction.

In an article entitled *Ambient Pressure Effect on Single-Bubble Sonoluminescence* by Dan et al. published in vol. 83, no. 9 of Physical Review Letters, the authors used a piezo-electric transducer to drive cavitation at the fundamental frequency of a glass cavitation chamber. This apparatus was used to study the effects of ambient pressure on bubble dynamics and single bubble sonoluminescence.

A variety of cavitation systems have been designed, many of which utilize partially filled cavitation chambers. As a result of the free liquid interface, it is often difficult to achieve the desired pressure within the cavitation fluid, especially if the cavitation fluid has a high vapor pressure. The present invention overcomes this problem.

SUMMARY OF THE INVENTION

The present invention provides a method and apparatus for monitoring a temperature difference between two regions within a cavitation system. The system's cavitation chamber is partially or completely filled with cavitation fluid, the amount that the system is filled controlling whether a cavitation fluid free surface is formed within the cavitation chamber or a conduit coupled to the chamber. Regardless of whether the region of the system above the cavitation fluid free surface is within the chamber or within the conduit, a temperature difference is created between this region and the cavitation fluid within the cavitation chamber. The temperature difference between these two regions is monitored by monitoring the temperature of each region. The temperature difference can be created by either heating the region above the cavitation fluid free surface, cooling the cavitation fluid, or both.

A further understanding of the nature and advantages of the present invention may be realized by reference to the remaining portions of the specification and the drawings.

DESCRIPTION OF THE SPECIFIC EMBODIMENTS

Figure 1:
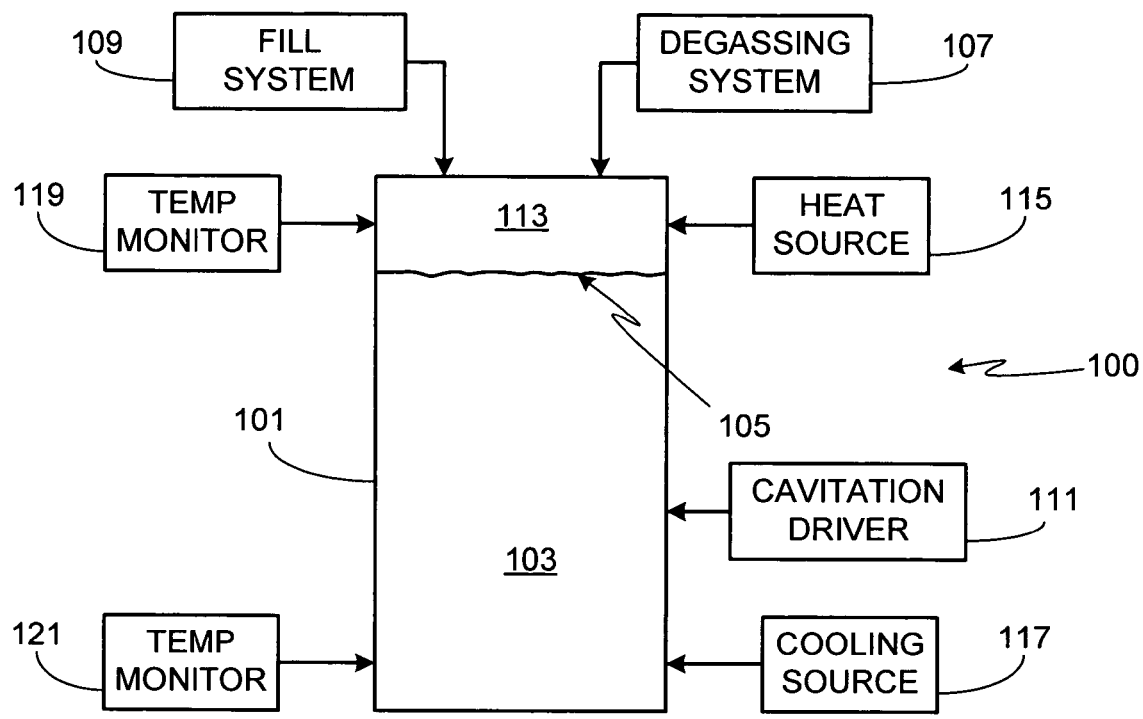
FIG. 1 is a conceptual illustration of the principal elements of a cavitation system utilizing the invention.

FIG. 1 is a conceptual illustration of a cavitation system 100. System 100 includes a cavitation chamber 101 which, during operation, contains a suitable cavitation fluid 103. As illustrated, chamber 101 is not completely full of cavitation fluid 103, thereby creating a free surface 105.

In the preferred embodiment of the invention, chamber 101 is a cylindrical chamber. It should be appreciated, however, that chamber 101 can utilize other configurations which are typically selected to accommodate a specific cavitation process and its corresponding process parameters (e.g., cavitation fluid, pressure, temperature, reactants, etc.). Examples of other configurations include spherical chambers, hourglass-shaped chambers, conical chambers, cubical chambers, rectangular chambers, irregularly-shaped chambers, etc. An example of a cylindrical cavitation chamber is provided in co-pending U.S. patent application Ser. No. 11/038,344, filed Jan. 18, 2005, entitled Fluid Rotation System for a Cavitation Chamber, the entire disclosure of which is incorporated herein for any and all purposes. One method of fabricating a spherical chamber is described in detail in co-pending U.S. patent application Ser. No. 10/925,070, filed Aug. 23, 2004, entitled Method of Fabricating a Spherical Cavitation Chamber, the entire disclosure of which is incorporated herein for any and all purposes. Examples of hourglass-shaped chambers are provided in co-pending U.S. patent application Ser. No. 11/140,175, filed May 27, 2005, entitled Hourglass-Shaped Cavitation Chamber, and Ser. No. 11/149,791, filed Jun. 9, 2005, entitled Hourglass-Shaped Cavitation Chamber with Spherical Lobes, the entire disclosures of which are incorporated herein for any and all purposes.

Chamber 101 can be fabricated from any of a variety of materials, depending primarily upon the desired operating pressure and temperature of the chamber and system. In order to simplify viewing of the sonoluminescence phenomena, chamber 101 can be fabricated from a relatively fragile and transparent material such as glass, borosilicate glass, or quartz glass (e.g., Pyrex®). Alternately chamber 101 can be fabricated from a more robust material (e.g., 17-4 precipitation hardened stainless steel) and one which is preferably machinable, thus simplifying fabrication. Preferably the selected chamber material is relatively corrosion resistant to the intended cavitation fluid, thus allowing the chamber to be used repeatedly.

The selected dimensions of chamber 101 depend primarily on the intended use of the chamber, although the cost of the cavitation fluid, chamber fabrication issues, operating temperature and cavitation driver capabilities also influence the preferred dimensions of the chamber for a specific process. In general, small chambers are preferred for situations in which it is desirable to limit the amount of the cavitation medium or in which driver input energy is limited while large chambers (e.g., 10 inches or greater) are preferred as a means of simplifying experimental set-up and event observation or when high energy reactions are being driven within the chamber. Thick chamber walls are preferred in order to accommodate high pressures.

A degassing system 107 is coupled to chamber 101. As described in the prior art, in order to achieve high intensity cavity implosions within the cavitation chamber, the cavitation medium must first be adequately degassed. The present invention is not limited to a particular degassing technique, and the techniques described below are for illustrative purposes only.

Degassing is preferably performed with a vacuum pump and may or may not include other degassing techniques such as low level cavitation, neutron bombardment, etc. Preferably the cavitation medium is degassed within cavitation chamber 101. Alternately the cavitation medium can be degassed prior to filling chamber 101. Alternately the cavitation medium can be degassed initially outside of chamber 101 and then again within chamber 101.

A cavitation medium filling system 109 is coupled to chamber 101. Filling system 109 may be comprised of a simple fill tube, a separate fluid reservoir, or other filling means. Although not required, system 109 may include a circulatory system, such as that described in co-pending U.S. patent application Ser. No. 11/001,720, filed Dec. 1, 2004, entitled Cavitation Fluid Circulatory System for a Cavitation Chamber, the disclosure of which is incorporated herein for any and all purposes. Other components that may or may not be coupled to the cavitation medium filling system include bubble traps, cavitation fluid filters, and heat exchange systems. Further descriptions of some of these variations are provided in co-pending U.S. patent application Ser. No. 10/961,353, filed Oct. 7, 2004, entitled Heat Exchange System for a Cavitation Chamber, the disclosure of which is incorporated herein for any and all purposes.

One or more drivers 111 are coupled to chamber 101, driver(s) 111 being used to drive the desired cavitation process within chamber 101. Clearly the invention is not limited to a specific number, type, mounting technique or mounting location for the driver(s). Examples of suitable drivers are given in co-pending U.S. patent application Ser. No. 10/931,918, filed Sep. 1, 2004, entitled Acoustic Driver Assembly for a Spherical Cavitation Chamber; Ser. No. 11/123,388, filed May 5, 2005, entitled Acoustic Driver Assembly With Recessed Head Mass Contact Surface; Ser. No. 11/123,381, filed May 6, 2005, entitled Acoustic Driver Assembly With Restricted Contact Area; and Ser. No. 11/068,080, filed Feb. 28, 2005, entitled Hydraulic Actuated Cavitation Chamber, the disclosures of which are incorporated herein in their entirety for any and all purposes.

In order to achieve high energy density (e.g., temperature) cavitation induced implosions, it is critical that cavitation fluid 103 be sufficiently degassed. Without sufficient degassing, gas within the cavitation fluid will impede the cavitation process by decreasing the rate of collapse of the cavitating bubbles (i.e., cushioning). Accordingly, in addition to evacuation, various techniques such as low energy cavitation and neutron bombardment can be used during the degassing process to further reduce the amount of gas trapped within the cavitation fluid. It will be understood that the term gas, as used herein, refers to any of a variety of gases that are trapped (i.e., dissolved) within the cavitation fluid, these gases typically reflecting the gases contained within air (e.g., oxygen, nitrogen, etc.). In contrast, vapor only refers to molecules of the cavitation fluid that are in the gaseous phase.

In addition to properly conditioning the cavitation fluid through degassing, the inventor has found that it is advantageous to create a condition in which volume 113 is at a higher temperature than cavitation liquid 103. As a result of this temperature difference, the vapor pressure above the liquid is greater than the vapor pressure of the liquid, thus suppressing boiling of the cavitation liquid. This, in turn, leads to higher energy density cavity implosions and the ability to successively cavitate larger cavities. Although the system will attempt to reach equilibrium through a vaporization/condensation process, by continually heating volume 113 and/or continually cooling cavitation liquid 103, this non-equilibrium state can be maintained indefinitely.

In order to obtain the desired temperature difference between volume 113 and cavitation liquid 103, preferably a heat source 115 is thermally coupled to the upper portion of chamber 101 such that it preferentially heats volume 113 above interface 105. The inventor has found that although the method of heating volume 113 is relatively unimportant, it is desirable to use a technique that is both energy efficient and does not unnecessarily heat cavitation fluid 103. More importantly, the technique used to mount heat source 115 should be selected to minimize the damping of the acoustic energy coupled into the chamber from cavitation driver(s) 111.

Although any of a variety of heat sources can be used for source 115 (e.g., hot air, resistive heaters, etc.), preferably heat source 115 is comprised of one or more resistive heaters mounted in close proximity to the exterior surface of volume 113 of chamber 101. As this approach does not require that source 115 be mechanically coupled to chamber 101, it does not dampen the acoustic energy from driver(s) 111. Alternately, source 115 (e.g., one or more resistive heaters) can be bonded to the exterior surface of chamber 101 using a thermally conductive adhesive/epoxy. This approach is not preferred, however, as it will dampen the acoustic energy from the driver(s). Heat source 115 can also be placed within volume 113, however this approach is also not preferred as it requires interconnects passing through the chamber wall and the heater must be able to tolerate the environment within the chamber.

As one aspect of the invention is creating a temperature difference between volume 113 and fluid 103, preferably in addition to heating source 115, a cooling source 117 is thermally coupled to cavitation fluid 103. Any of a variety of coolers can be used for source 117, such as thermoelectric coolers (i.e., TECs), refrigeration coils, refrigerated chambers, directed cold air sources, etc. Cooling source 117 can either be in direct contact with fluid 103, or indirect contact with fluid 103 (e.g., through a wall of chamber 101). Indirect contact is preferred as it avoids interconnects passing through chamber walls as well as potential cavitation fluid contamination and cavitation disruption.

There are a number of benefits of utilizing cooling source 117 in conjunction with heat source 115. First, the use of both a heat source and a cooling source simplifies the system's ability to maintain the non-equilibrium state in which the vapor pressure above surface 105 is greater than that of cavitation liquid 103. Second, cooling source 117 allows cavitation fluid 103 to be maintained at a temperature less than the ambient temperature, leading to more rapid vapor condensation, and thus more intense cavity implosions during the cavitation process. Third, by actively heating region 113 with heater 115 and actively cooling fluid 103 with cooler 117, the temperatures of the two regions (i.e., 113 and 103) as well as the temperature difference between the two regions can be accurately maintained at the desired levels. This is an extremely beneficial aspect of the invention once particular operating temperatures and desired temperature differences are determined. For example, the inventor has determined that for a cavitation fluid comprised of deuterated acetone, preferably during cavitation the temperature of the fluid is maintained at approximately 0° C. while the temperature of region 113 is maintained at a temperature of at least 10° C. higher, and preferably 20° C. higher, than that of the fluid.

Given the sensitivity of the cavitation process to both cavitation fluid temperature and the temperature difference between the cavitation fluid and the region above the fluid's free surface, and given the sensitivity of some cavitation chamber materials (e.g., glass) to temperature differences, it is important to monitor the temperature of fluid 103 and region 113 in order to achieve the desired temperatures without overstressing the chamber through excessive temperature variations. Accordingly in the preferred embodiment of the invention, a temperature monitor 119 is thermally coupled to region 113 and a second temperature monitor 121 is thermally coupled to cavitation fluid 103. Preferably monitors 119 and 121 are comprised of thermocouples or thermistors and are thermally coupled to the exterior surface of chamber 101, adjacent to the regions of interest. This approach provides only an indirect measure of the temperatures of interest as the temperature monitors are not in direct contact with either region 113 or fluid 103. Indirect contact through the chamber walls is preferred, however, over direct contact with the fluid of interest (i.e., vapor within region 113 or fluid 103) as it avoids issues such as chamber feed-throughs for the monitors, potential cavitation fluid contamination and possible cavitation disruption.

Although FIG. 1 and the accompanying description provides sufficient information to enable application of the invention, a few preferred embodiments are provided below to illustrate some of the possible design variations for the chamber, heater, cooler, and temperature monitors. As the invention is not limited to a specific cavitation filling and/or circulatory system, nor is it limited to a specific degassing system, these aspects of each cavitation system are not shown in the following figures, thereby simplifying the figures. Similarly, as the invention is not limited to a specific cavitation driver(s), only an exemplary driver is shown in each figure. Lastly it will be appreciated that heater 115 or the combination of heater 115 and cooler 117 can be used without temperature monitors 119 and/or 121, and conversely, temperature monitors 119 and/or 121 can be used without heater 115, cooler 117 or the combination of heater 115 and cooler 117.

Figure 2:
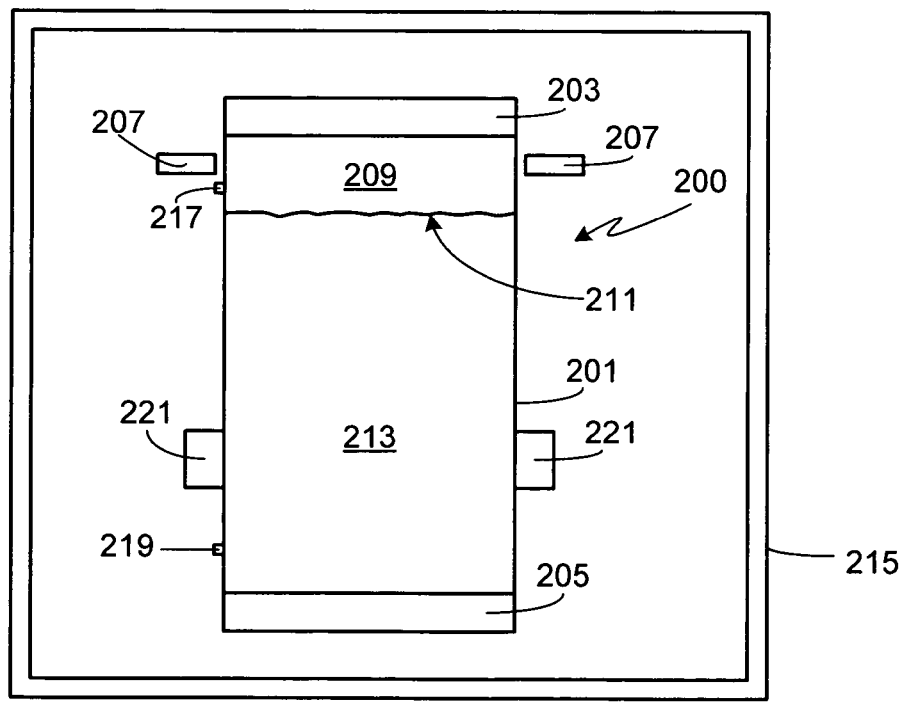
FIG. 2 is a cross-sectional view of a cylindrical cavitation chamber with end caps.

FIG. 2 is an illustration of a preferred embodiment 200 comprised of a cylinder 201 and a pair of end caps 203/205. In one configuration of this embodiment, end caps 203/205 are made of a metal (e.g., aluminum) while cylinder 201 is made of a glass. The use of a glass for cylindrical chamber section 201 allows easy visual monitoring of the cavitation occurring within the chamber during operation of the cavitation system. A pair of heaters (e.g., resistive heater elements) 207 are mounted within close proximity to the outside surface of cylinder 201, adjacent to region 209 and above cavitation fluid free surface 211. It will be appreciated that other heater mounting methods can be used as previously noted, for example attaching the heater to, or within, upper end cap 203. As previously noted, preferably in addition to heating the region above the cavitation fluid free surface 211, the chamber includes means for actively cooling cavitation fluid 213. Although a cooler can be attached to, or mounted within, lower end cap 205, preferably cavitation chamber 200 is mounted within a refrigerated housing 215.

In order to monitor the temperature of region 209, preferably a temperature monitor (e.g., thermocouple or thermistor) 217 is thermally coupled to the upper portion of chamber section 201, immediately adjacent to region 209. Similarly, in order to monitor the temperature of cavitation fluid 213, preferably a temperature monitor (e.g., thermocouple or thermistor) 219 is thermally coupled to the lower portion of chamber section 201, immediately adjacent to fluid 213. Note that temperature monitors 217/219, or additional monitors, can also be mounted to, or within, end caps 203/205. In this embodiment, driver 221 is comprised of a ring of piezoelectric material, preferably bonded to chamber 200 with an epoxy or other adhesive.

Figure 3:
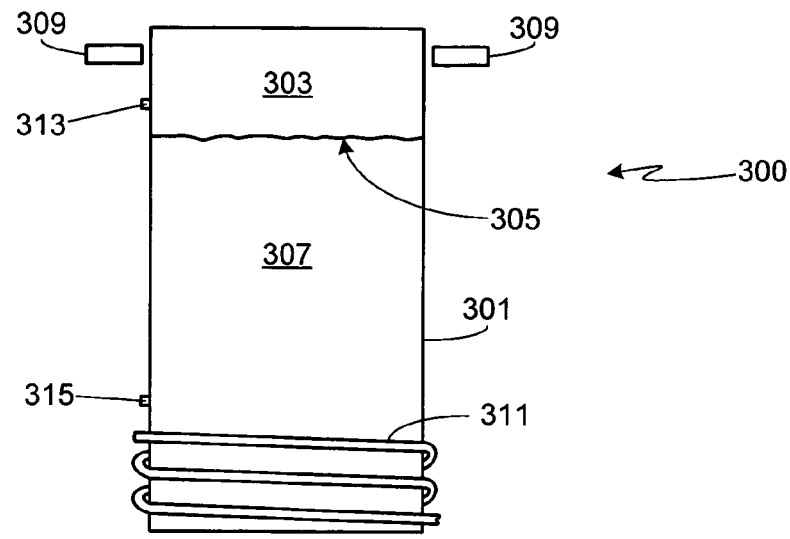
FIG. 3 is a cross-sectional view of a cylindrical cavitation chamber without end caps.

FIG. 3 is an illustration of a cylindrical chamber 300. Chamber 300 may be comprised of a single piece 301, as shown, or multiple pieces (e.g., cylindrical section and end caps). Cylinder 301 can be comprised of either a fragile material (e.g., glass) or a more robust material (e.g., stainless steel). Materials such as glass have the benefit of allowing the cavitation process to be easily observed without including a port within the chamber. The disadvantage of a fragile material is that it is more likely to break, for example due to handling, temperature differences, or even the cavitation process itself. A material that is not very thermally conductive is preferred as it helps to achieve the desired temperature difference between region 303, above liquid-vapor interface 305, and cavitation fluid 307.

In this embodiment one or more heaters 309 surround upper region 303. Preferably heater(s) 309 is a resistive heater. As previously noted, preferably in addition to heating the region above the cavitation fluid free surface 305, the chamber includes means for actively cooling the cavitation fluid itself. In this embodiment a cooling tube 311 is coiled around the lower section of chamber 301, cooling tube 311 coupled to a mechanical refrigeration system (not shown).

In order to monitor the temperature of region 303, preferably at least one temperature monitor (e.g., thermocouple) 313 is thermally coupled to the upper portion of chamber 301, immediately adjacent to region 303. Additionally, preferably at least one temperature monitor (e.g., thermocouple) 315 is thermally coupled to the lower portion of chamber 301, thus providing a means of monitoring the temperature of cavitation fluid 307.

In order to improve the efficiency of the heating system, and the cooling system if used, it is desirable to bring the respective heaters/coolers as well as the temperature monitors into close proximity with the region of interest. It is also more efficient to thermally isolate the heaters, and coolers if used, from the chamber structure. One technique for accomplishing these goals is illustrated in FIGS. 4 and 5, this technique applicable to a heater for the region above the cavitation fluid interface, a cooler for the cavitation fluid, or a temperature monitor for use with either.

Figures 4, 5:
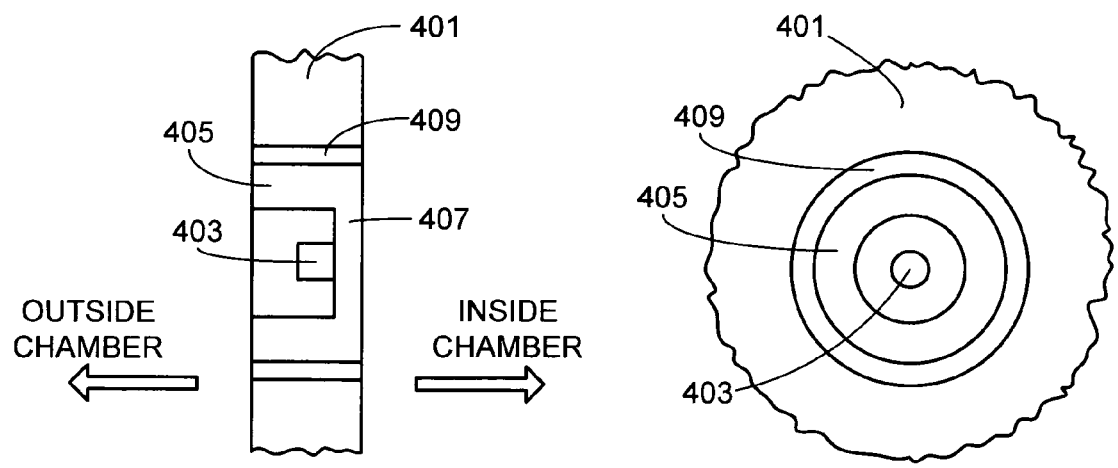
FIG. 4 is a cross-sectional view of a portion of a cavitation chamber wall which illustrates a thermal isolation assembly.
FIG. 5 is a front view of the portion of the cavitation chamber wall shown in FIG. 4.

FIG. 4 is a cross-sectional view of a portion of a chamber wall 401 while FIG. 5 provides an external chamber view of the same chamber wall portion. Device 403 represents either a heater (e.g., resistive heater, etc.), a cooler (e.g., TEC cooler, etc.) or a temperature monitor (e.g., thermocouple, etc.). A plug 405, preferably comprised of a thermally conductive material, provides the mounting location for device 403. Although device 403 can simply be mounted to the external surface of plug 405, preferably device 403 is mounted to a hollowed out portion of plug 405 as shown, thus minimizing the thickness of wall section 407 which separates device 403 from the inside of the cavitation chamber. Preferably plug 405 is mounted within a thermally non-conductive member 409 which is, in turn, mounted within chamber wall 401. If chamber wall 401 is comprised of a thermally non-conductive material, plug 405 can be mounted directly within chamber wall 401.

Figure 6:
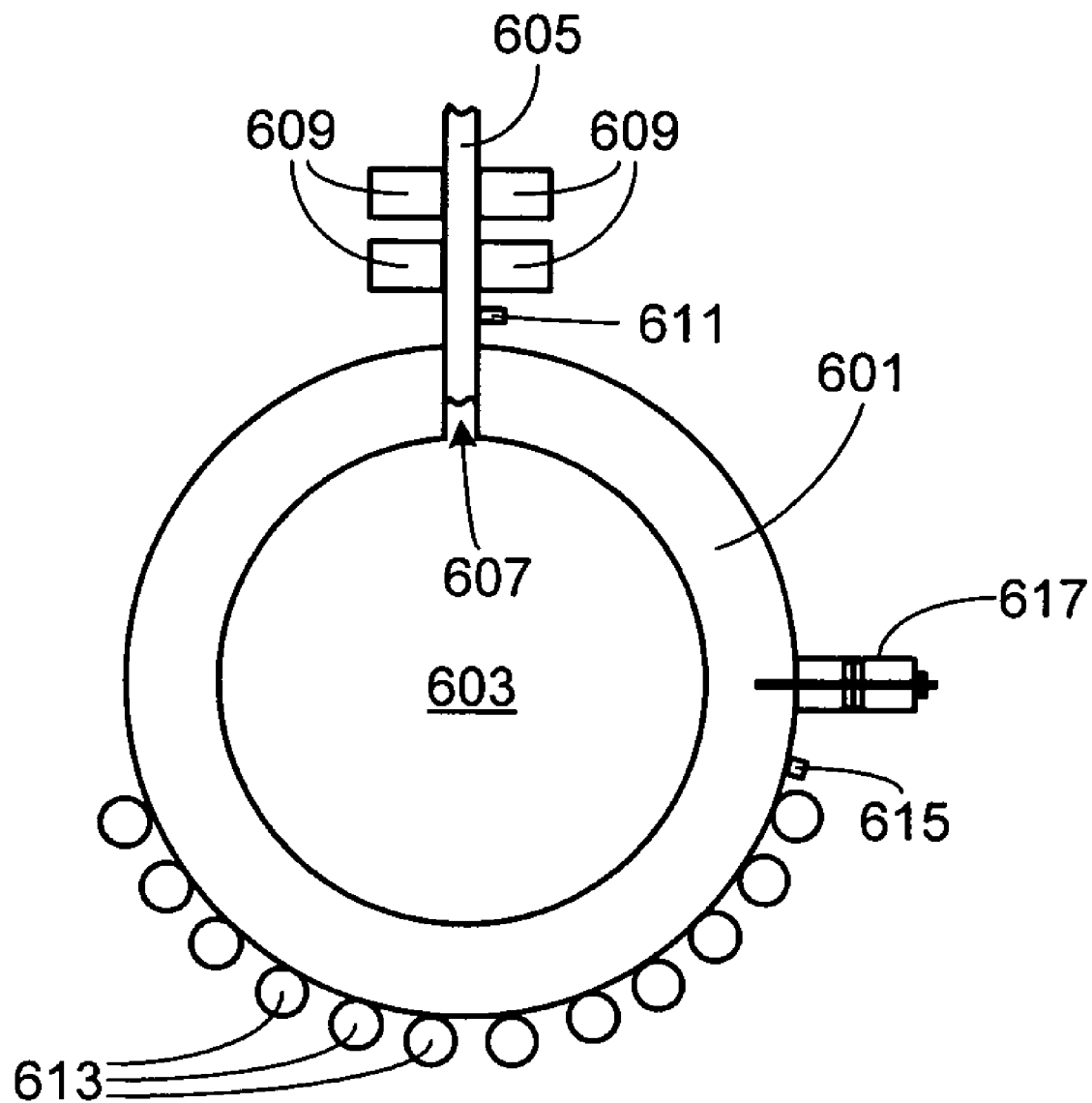
FIG. 6 is a cross-sectional view of a spherical cavitation chamber.

As previously described, the present invention is not limited to a particular cavitation chamber configuration, nor is it limited to specific heaters and/or coolers and/or temperature monitors. For example, FIG. 6 is a cross-sectional view of a spherical chamber 601 filled with cavitation fluid 603. A conduit 605 passes through the chamber wall and provides access to the inside of chamber 601. Conduit 605 is typically used during chamber filling, degassing, etc. In this embodiment, the cavitation fluid free surface 607 is within conduit 605 as shown. One or more heaters 609 heat the vapor within conduit 605. Preferably a temperature monitor 611 is attached to conduit 605 as well. Although not required, in this embodiment the lower portion of chamber 601 is wrapped with cooling coils 613 which are coupled to a mechanical refrigeration system (not shown). The temperature of the chamber is monitored with one or more temperature monitors 615. An acoustic driver 217 is shown coupled to chamber 601.

As will be understood by those familiar with the art, the present invention may be embodied in other specific forms without departing from the spirit or essential characteristics thereof. Accordingly, the disclosures and descriptions herein are intended to be illustrative, but not limiting, of the scope of the invention which is set forth in the following claims.

What is claimed is:

1. A method of monitoring a temperature difference within a cavitation chamber, the method comprising the steps of: partially filling the cavitation chamber with a cavitation fluid, wherein said partial filling step creates a cavitation fluid free surface within the cavitation chamber; creating the temperature difference between a first region of the cavitation chamber and a second region of the cavitation chamber, wherein said first region is above said cavitation fluid free surface and said second region is below said cavitation fluid free surface; inducing cavitation of the cavitation fluid by introducing acoustic energy into the cavitation fluid; monitoring a first temperature corresponding to said first region of said cavitation chamber; and monitoring a second temperature corresponding to said second region of said cavitation chamber.

2. The method of claim 1, wherein said temperature difference creating step further comprises the step of heating said first region of the cavitation chamber.

3. The method of claim 2, wherein said heating step heats said first region to a first temperature that is at least 10° C. higher than said second temperature.

4. The method of claim 1, wherein said temperature difference creating step further comprises the step of cooling said second region of the cavitation chamber.

5. The method of claim 4, wherein said cooling step cools said second region to a second temperature that is at least 10° C. lower than said first temperature.

6. The method of claim 1, wherein said temperature difference creating step further comprises the steps of heating said first region of the cavitation chamber and cooling said second region of the cavitation chamber.

7. The method of claim 6, wherein the temperature difference created by the combination of said heating step and said cooling step is such that said first temperature is at least 10° C. higher than said second temperature.

8. The method of claim 1, further comprising the step of degassing said cavitation chamber after completion of said partial filling step.

9. The method of claim 1, further comprising the step of cavitating said cavitation fluid within said cavitation chamber after completion of said temperature difference creating step.

10. The method of claim 1 further comprising suppressing boiling of the cavitation fluid wherein said suppressing boiling results from said creating the temperature difference between the first region of the cavitation chamber and the second region of the cavitation chamber.

11. A method of monitoring a temperature difference within a cavitation system, the method comprising the steps of: filling a cavitation chamber with a cavitation fluid, wherein said filling step creates a cavitation fluid free surface within a conduit coupled to said cavitation chamber, wherein during operation of said cavitation system said cavitation chamber is open to said conduit; creating the temperature difference between a region of said conduit and a region of said cavitation chamber, wherein said region of said conduit is above said cavitation fluid free surface and said region of said cavitation chamber is below said cavitation fluid free surface; inducing cavitation of the cavitation fluid by introducing acoustic energy into the cavitation fluid; monitoring a first temperature corresponding to said region of said conduit; and monitoring a second temperature corresponding to said region of said cavitation chamber.

12. The method of claim 11, wherein said temperature difference creating step further comprises the step of heating said region of said conduit.

13. The method of claim 12, wherein said heating step heats said region of said conduit to a first temperature that is at least 10° C. higher than said second temperature.

14. The method of claim 11, wherein said temperature difference creating step further comprises the step of cooling said region of said cavitation chamber.

15. The method of claim 14, wherein said cooling step cools said region of said cavitation chamber to a second temperature that is at least 10° C. lower than said first temperature.

16. The method of claim 11, wherein said temperature difference creating step further comprises the steps of heating said region of said conduit and cooling said region of said cavitation chamber.

17. The method of claim 16, wherein the temperature difference created by the combination of said heating step and said cooling step is such that said first temperature is at least 10° C. higher than said second temperature.

18. The method of claim 11, further comprising the step of degassing said cavitation chamber after completion of said filling step.

19. The method of claim 18, further comprising the step of cavitating said cavitation fluid within said cavitation chamber after completion of said temperature difference creating step.

20. The method of claim 11 further comprising suppressing boiling of the cavitation fluid wherein said suppressing boiling results from said creating the temperature difference between the region of said conduit and the region of said cavitation chamber.

* * * * *